(12) United States Patent
Chu (10) Patent No.: US 10,531,689 B2
(45) Date of Patent: Jan. 14, 2020

(54) MULTIFUNCTIONAL ELECTRONIC CIGARETTE AND MULTIFUNCTIONAL PORTABLE ELECTRONIC DEVICE

(71) Applicant: Nuvoton Technology Corporation, Hsinchu (TW)

(72) Inventor: Ping-Ying Chu, Hsinchu (TW)

(73) Assignee: NUVOTON TECHNOLOGY CORPORATION, Hsinchu (TW)

( * ) Notice: Subject to any disclaimer, the term of this patent is extended or adjusted under 35 U.S.C. 154(b) by 177 days.

(21) Appl. No.: 15/820,042

(22) Filed: Nov. 21, 2017

(65) Prior Publication Data

US 2018/0228218 A1 Aug. 16, 2018

(30) Foreign Application Priority Data

Feb. 10, 2017 (TW) .............................. 106104535 A (51) Int. Cl.

| *A24F 13/00* | (2006.01) |
|---|---|
| *A24F 17/00* | (2006.01) |
| *A24F 25/00* | (2006.01) |
| *A24F 47/00* | (2006.01) |
| *G01N 33/497* | (2006.01) |
| *G01N 33/00* | (2006.01) |
| *A61B 5/08* | (2006.01) |
| *A61B 5/00* | (2006.01) |

(52) U.S. Cl.
CPC ....... *A24F 47/008* (2013.01); *G01N 33/4972* (2013.01); *A61B 5/082* (2013.01); *A61B 5/4845* (2013.01); *G01N 33/0009* (2013.01)

(58) Field of Classification Search
CPC . A24F 47/008; A24F 47/002; G01N 33/4972; B01F 13/002; B01F 15/00519
USPC .................................................. 131/328, 329
See application file for complete search history.

(56) References Cited

U.S. PATENT DOCUMENTS

| 2015/0335072 A1* | 11/2015 | Giller .................. | F21V 33/0004 |
|---|---|---|---|
| | | | 131/328 |
| 2016/0363570 A1* | 12/2016 | Blackley ............ | G01N 33/0006 |
| 2017/0123878 A1* | 5/2017 | Chu ..................... | G06F 11/0736 |
| 2018/0020734 A1* | 1/2018 | Angstead .............. | A24F 47/008 |

\* cited by examiner

*Primary Examiner* — Hae Moon Hyeon
(74) *Attorney, Agent, or Firm* — Muncy, Geissler, Olds & Lowe, P.C.

(57) ABSTRACT

The present is a multifunctional electronic cigarette. In the multifunctional electronic cigarette, an interchangeable member can include one of an E-liquid cassette having an atomizing component, an alcohol detecting device and a LED device; a processing module can control the power supply module to respectively apply an initial voltage and a test voltage to the connection assembly in sequential order, and calculate an operational resistance of the interchangeable member during the process of applying voltages, and then control the power supply module to generate operation voltage and current to the interchangeable member according to the operational resistance. The operational resistance is resistance of the interchangeable member which is executing a main operational function thereof. As a result, the multifunctional electronic cigarette can have improved extendibility.

14 Claims, 7 Drawing Sheets

MULTIFUNCTIONAL ELECTRONIC CIGARETTE AND MULTIFUNCTIONAL PORTABLE ELECTRONIC DEVICE

CROSS-REFERENCE TO RELATED APPLICATION

This application claims priority from Taiwan Patent Application No. 106104535 filed on Feb. 10, 2017 at the Taiwan Intellectual Property Office, the content of which is hereby incorporated by reference in its entirety for all purposes.

BACKGROUND OF THE INVENTION

1. Field of the Invention

The present disclosure relates to a multifunctional electronic cigarette and a multifunctional portable electronic device. More particularly, the present disclosure relates to a multifunctional electronic cigarette capable of detecting operational resistance or identification data of an expansion device.

2. Description of the Related Art

Conventional electronic cigarette device is used to perform electronic cigarette function only. Generally, according to healthy research, 80% of people having smoking habits also have habits of drinking alcoholic beverage possibly. In order to prevent drunk driving, the driver must detect blood alcohol concentration before driving; for this reason, the person having smoking habits may also need to carry an alcohol detector for frequent use.

However, when the electronic cigarette device is combined with the alcohol detector for purpose of detecting blood alcohol concentration, the combined device becomes heavier and larger, and it may affect the user's willingness to use and carry.

SUMMARY OF THE INVENTION

In order to solve above-mentioned problem, the present disclosure is to provide a multifunctional electronic cigarette and a multifunctional portable electronic device.

According to a first aspect, the present disclosure provides a multifunctional electronic cigarette including an outer shell member, a processing module, a power supply module, a connection assembly and an interchangeable member. The processing module is disposed in the outer shell member. The power supply module is disposed in the outer shell member and electrically coupled to the processing module. The connection assembly is electrically coupled to the power supply module and the processing module, and fixed on and exposed out of an end of the outer shell member. The interchangeable member is electrically coupled to the connection assembly, and includes one of an electronic-liquid (E-liquid) cassette having an atomizing component, an alcohol detecting device and a light-emitting diode(LED) device. The processing module is configured to control the power supply module to respectively apply an initial voltage and a test voltage to the connection assembly in sequential order, and calculate an operational resistance of the interchangeable member during the process of applying voltages, and then control the power supply module to generate operation voltage and current to the interchangeable member according to the operational resistance. The operational resistance is resistance of the interchangeable member which is executing a main operational function thereof.

Preferably, during the process of applying the voltage form the initial voltage to the test voltage, the operational resistance of the LED device is dropped after the voltage exceeds a barrier voltage which has a value between the initial voltage and the test voltage.

Preferably, the operational resistance of the alcohol detecting device is higher than that of the E-liquid cassette.

Preferably, the connection assembly comprises an exhaust gas oxygen(EGO) connector or a 510 connector.

Preferably, the processing module stores a plurality of resistance ranges and a plurality of device driver programs respectively corresponding to the plurality of resistance ranges, and the processing module selects and executes one of the plurality of device driver programs according to the operational resistance and the plurality of resistance ranges, thereby controlling the power supply module to output the operation voltage and current.

Preferably, the alcohol detecting device generates different sensing resistances for different blood alcohol concentrations.

According to a second aspect, the present disclosure provides a multifunctional electronic cigarette including an outer shell member, a processing module, a power supply module, at least one data transmission line, a connection assembly and an interchangeable member. The processing module is disposed in the outer shell member and configured to store a component definition table which records identification data and working mode data corresponding to the identification data. The power supply module is disposed in the outer shell member and electrically coupled to the processing module. The at least one data transmission line includes an end electrically coupled to the processing module. The connection assembly is electrically coupled to the power supply module and the processing module, fixed on and expose out of an end of the outer shell member, and includes at least one transmission part and an engagement part. The at least one transmission part is connected with other end of the data transmission line. The interchangeable member is combined with the engagement part to connect with the connection assembly by a rotation manner, and includes an E-liquid cassette which includes one of an atomizing component, an alcohol detecting device, a LED device, and a laser device. The processing module receives identification data of the interchangeable member through the at least one transmission part and the data transmission line, and the processing module compares the received identification data with the stored identification data to determine a type of the interchangeable member, and the processing module executes the working mode data corresponding to the determined type, to generate operation voltage and current for the interchangeable member.

Preferably, the working mode data comprises variations in strength and frequency of the operation voltage and current.

Preferably, the interchangeable member and the processing module are in communication with each other by a communication protocol.

Preferably, the processing module stores a plurality of resistance range and a plurality of device driver programs respectively corresponding to the plurality of resistance range, and the processing module selects and executes one of the plurality of device driver programs according to the operational resistance and the plurality of resistance ranges, thereby controlling the power supply module to output the operation voltage and current.

According to a third aspect, the present disclosure provides a multifunctional portable electronic device including: an outer shell member; a processing module disposed in the outer shell member; a power supply module disposed in the outer shell member and electrically coupled to the processing module; a connection assembly electrically coupled to the power supply module and the processing module, and fixed on and exposed out of an end of the outer shell member; and a plurality of interchangeable members selectively coupled to the connection assembly electrically, and including at least two of an E-liquid cassette having an atomizing component, an alcohol detecting device, and a LED device. In a detection mode, the processing module calculates an operational resistance of one of the plurality of the interchangeable members which is coupled to the connection assembly, and then controls, in a normal operation mode, the power supply module to generate operation voltage and current according to the operational resistance. The operational resistance is resistance of the interchangeable member which is executing a main operational function thereof.

Preferably, in the detection mode, the processing module controls the power supply module to respectively apply an initial voltage and a test voltage to the connection assembly in sequential order for calculation of the operational resistance.

Preferably, the operational resistance of the alcohol detecting device is higher than that of the E-liquid cassette.

Preferably, the connection assembly comprises an EGO connector or a 510 connector.

BRIEF DESCRIPTION OF THE DRAWINGS

The structure, operating principle and effects of the present disclosure will be described in detail by way of various embodiments which are illustrated in the accompanying drawings.

DETAILED DESCRIPTION OF THE PREFERRED EMBODIMENTS

The following embodiments of the present disclosure are herein described in detail with reference to the accompanying drawings. These drawings show specific examples of the embodiments of the present invention. It is to be understood that these embodiments are exemplary implementations and are not to be construed as limiting the scope of the present invention in any way. Further modifications to the disclosed embodiments, as well as other embodiments, are also included within the scope of the appended claims. These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts.

It is to be understood that, although the terms 'first', 'second', 'third', and so on, may be used herein to describe various elements, these elements should not be limited by these terms. These terms are used only for the purpose of distinguishing one component from another component. Thus, a first element discussed herein could be termed a second element without altering the description of the present invention. As used herein, the term "or" includes any and all combinations of one or more of the associated listed items.

Figure 1:
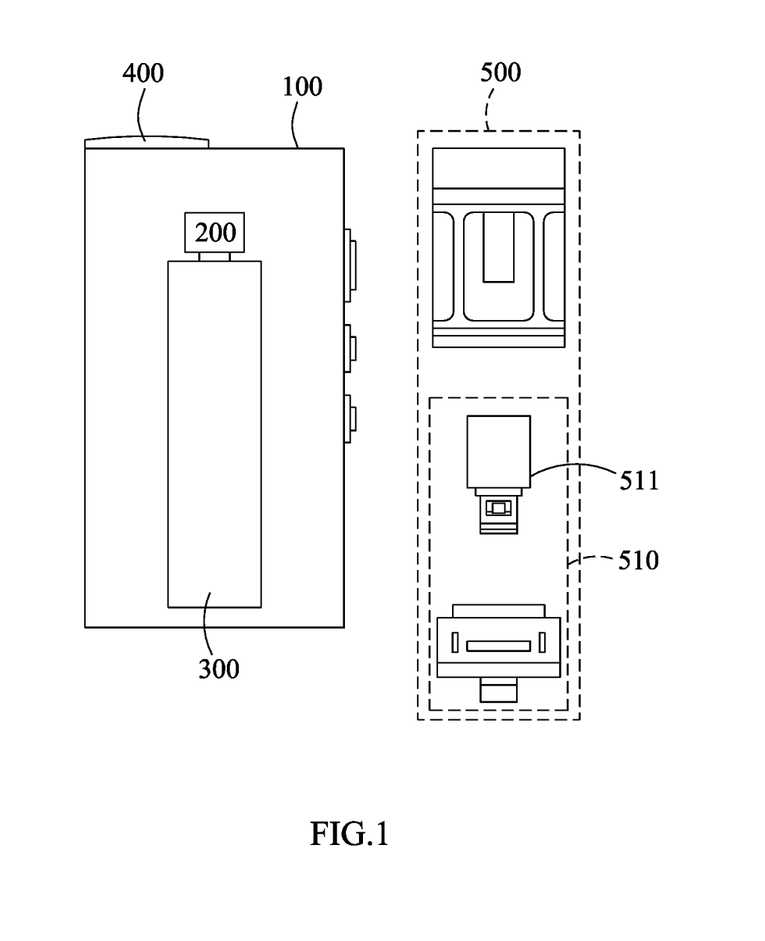
FIG. 1 is a schematic view of a first aspect of the multifunctional electronic cigarette of the present disclosure.
Figure 2:
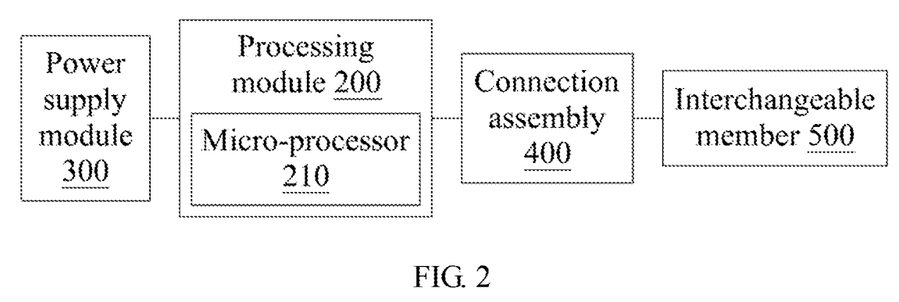
FIG. 2 is a block diagram of the first aspect of the multifunctional electronic cigarette of the present disclosure.

The following refers to FIGS. 1 and 2, which are schematic view and block diagram of a first aspect of a multifunctional electronic cigarette of the present disclosure, respectively.

The multifunctional electronic cigarette includes an outer shell member 100, a processing module 200, a power supply module 300, a connection assembly 400 and an interchangeable member 500. The processing module 200 is disposed inside the outer shell member 100, and includes a microprocessor 210 configured to control electronic components of the multifunctional electronic cigarette.

The power supply module 300 is disposed inside the outer shell member 100 and electrically coupled to the processing module 200. The processing module 200 can control the power supply module 300 to output voltage and current. The connection assembly 400 is electrically coupled to the power supply module 300 and the processing module 200, and fixed at and exposed out of an end of the outer shell member 100. The connection assembly 400 may include an EGO connector or a 510 connector which is commercially available. It should be noted that the term "510 connector" is a specification name of a common connector known in industry but not a reference number in the present disclosure. The interchangeable member 500 is electrically coupled to the connection assembly 400. The interchangeable member 500 may include an E-liquid cassette 510 having an atomizing component 511, an alcohol detecting device 520, or a LED device.

Under a condition that the interchangeable member 500 includes the E-liquid cassette 510 having the atomizing component, the user can assemble the E-liquid cassette 510 with the connection assembly 400 to form the electronic cigarette, and the power supply module 300 provides power to the atomizing component for atomization of E-liquid contained in the E-liquid cassette 510.

Similarly, under a condition that the interchangeable member 500 includes the alcohol detecting device 520, the user can assemble the alcohol detecting device 520 with the connection assembly 400 to form an alcohol detector, and the power supply module 300 can provide power to the alcohol detecting device 520, so that the user can blow into the alcohol detecting device 520 to detect the user's blood alcohol concentration. Similarly, under a condition that the interchangeable member 500 is the LED device, the user can assemble the LED device with the connection assembly 400 to form a LED flashlight for illumination.

The power supply manners and driving manners for aforementioned three interchangeable members are different from each other, and will be respectively described in the following paragraphs.

In order to determine whether the interchangeable member 500 includes one of the E-liquid cassette 510 having the atomizing component, the alcohol detecting device 520 and the LED device, the processing module 200 can, in a detection mode, control the power supply module 300 to output an initial voltage and a test voltage to the interchangeable member 500 in sequential order, and then calculate an operational resistance of the interchangeable member 500 during the period of the initial voltage to the test voltage. As a result, the processing module 200 can determine the type of the interchangeable member 500 according to the operational resistance, thereby driving the interchangeable member 500 by appropriate operation voltage and current in a normal operation mode. Preferably, the operational resistance is resistance of the interchangeable member 500 while the interchangeable member 500 performs a main operational function thereof in practice, but not resistance of a resistor element additionally disposed in the interchangeable member 500 for device identity recognition only.

Figure 3:
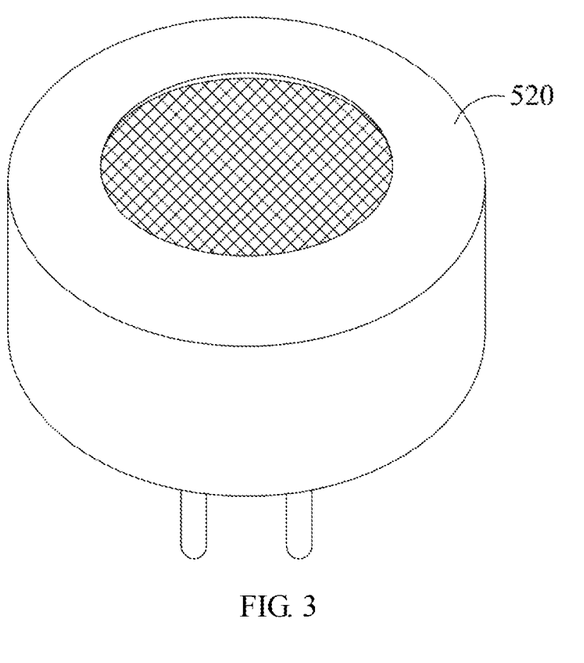
FIG. 3 is a schematic view of the multifunctional electronic cigarette served as an alcohol detecting device, in accordance with the present disclosure.
Figure 4:
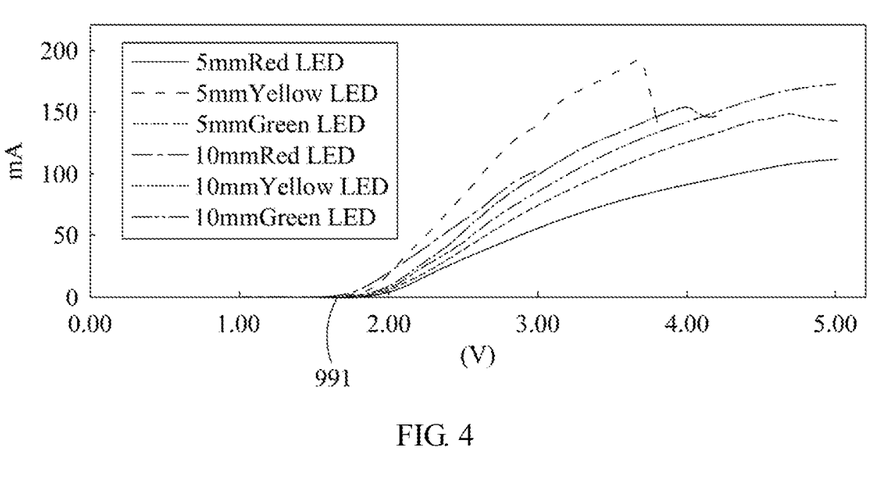
FIG. 4 is a curve diagram of a driving voltage for a LED device, in accordance with the present disclosure.

The following refers to FIGS. 3 and 4. FIG. 3 is a schematic view of the multifunctional electronic cigarette served as the alcohol detecting device, in accordance with the present disclosure, and FIG. 4 is a curve diagram of a driving voltage of the multifunctional electronic cigarette served as the LED device, in accordance with the present disclosure.

After detecting the operational resistance of the interchangeable member 500 in the detection mode, the processing module 200 of the present disclosure can generate appropriate operation voltage and current for the interchangeable member 500 in the normal operation mode according to the detected operational resistance. Different interchangeable members 500 have operational resistances significantly different from each other, for example, the E-liquid cassette 510 having the atomizing component may have the operational resistance lower than 10Ω, and the alcohol detecting device 520 may have the operational resistance higher than 500Ω. For this reason, during the process where the processing module 200 applies voltage from the initial voltage to the test voltage in the detection mode, when the processing module 200 detects that the operational resistance of the interchangeable members 500 is higher than 500Ω, the processing module 200 can determine the interchangeable members 500 to be the alcohol detecting device 520; otherwise, when the processing module 200 detects that the operational resistance of the interchangeable members 500 is lower than 10Ω, the processing module 200 can determine the interchangeable members 500 to be the E-liquid cassette 510.

As shown in FIG. 4, according to electric property of the LED device, the processing module 200 can determine whether the interchangeable member 500 is the LED device. During the process where the processing module 200 applies the voltage changed from the initial voltage to the test voltage in the detection mode, when the processing module 200 detects that the operational resistance of the LED device is dropped after the applied voltage exceeds a barrier voltage 991 which has a value between the initial voltage and the test voltage, the processing module 200 can determine that the interchangeable member 500 includes the LED device.

In order to quickly operate the interchangeable member 500 after the interchangeable member 500 is connected to the connection assembly 400, the processing module 200 can pre-store a plurality of resistance ranges and a plurality of device driver programs which respectively correspond to each other, so that the processing module 200 can compare the detected operational resistance and the plurality of resistance ranges, and execute one of the plurality of device driver programs according to a comparison result, thereby controlling the power supply module 300 to output appreciate operation voltage and current to the interchangeable member 500.

The alcohol detecting device 520 may have different operational resistance when detecting different alcohol concentration in a user's breath, for example, the operational resistance of the alcohol detecting device 520 may respectively be in a range of 3 kΩ to 30 kΩ, in a range of 1 kΩ to 10 kΩ, and in a range of 0.7 kΩ to 7 kΩ in response to 50 PPM of alcohol concentration, 300 PPM of alcohol concentration and 500 PPM of alcohol concentration, so that the processing module 200 can obtain the blood alcohol concentration according to the detected operational resistance. Different interchangeable members 500 require different operation voltages and currents, for example, the E-liquid cassette 510 having atomizing component is configured to heat and atomize the E-liquid continuously according to the temperature of the E-liquid; for this reason, the processing module 200 can select and execute one of the plurality of restored device driver programs according to the plurality of pre-stored resistance ranges and the detected operational resistance, to control the power supply module 300 to output appropriate operation voltage and current for the interchangeable members 500.

Figure 5:
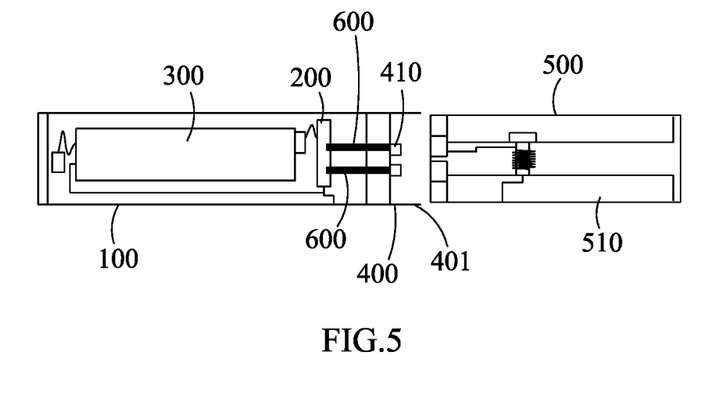
FIG. 5 is a schematic view of a second aspect of the multifunctional electronic cigarette of the present disclosure.
Figure 6:
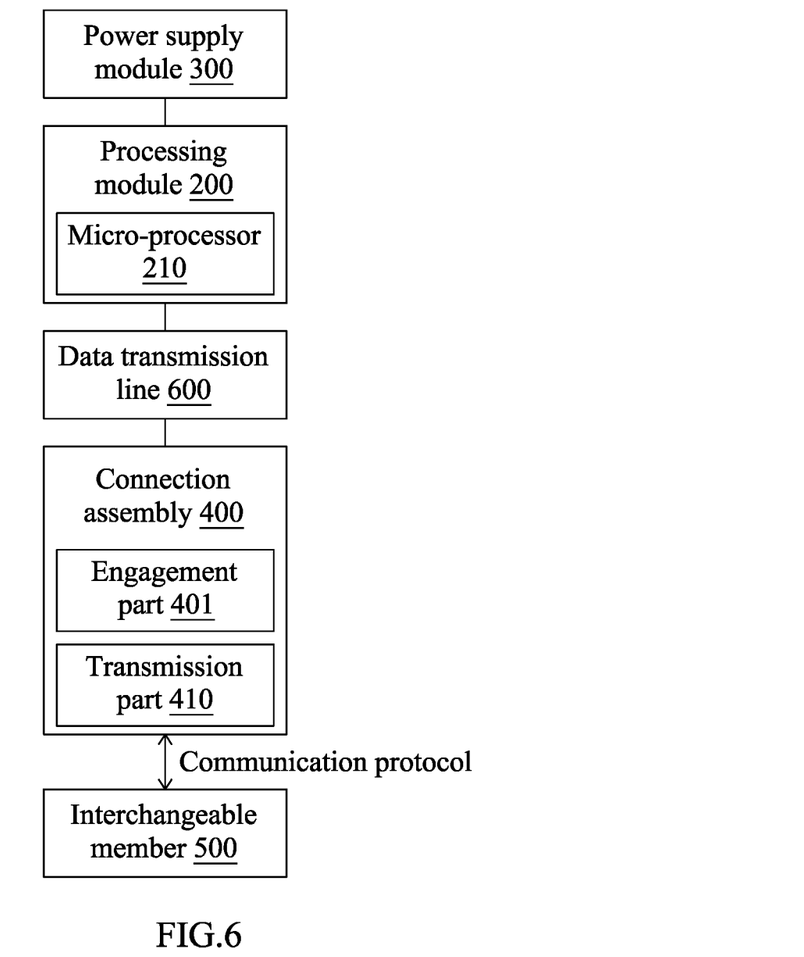
FIG. 6 is a block diagram of the second aspect of the multifunctional electronic cigarette of the present disclosure.
Figure 7:
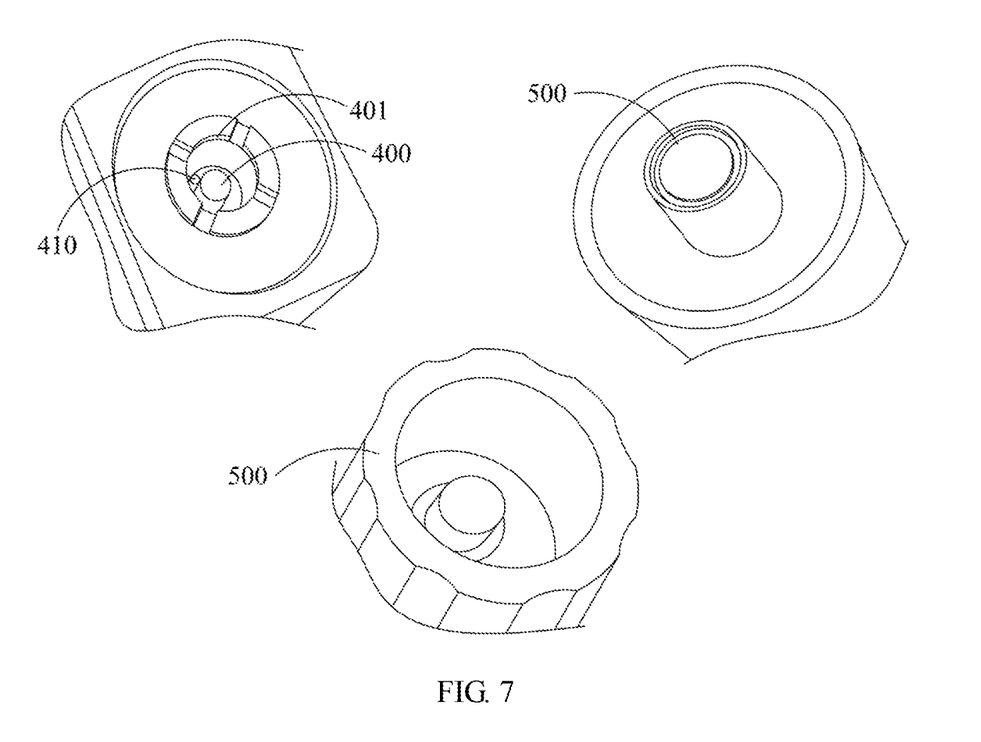
FIG. 7 is a schematic view of a connection assembly of the multifunctional electronic cigarette of the present disclosure.

The following refers to FIGS. 5 to 7, which are schematic view and block diagram of a second aspect of the multifunctional electronic cigarette of the present disclosure, and schematic view of a connection assembly of the multifunctional electronic cigarette of the present disclosure, respectively.

In the second aspect, the multifunctional electronic cigarette includes the outer shell member 100, the processing module 200, the power supply module 300, at least one data transmission line 600, a connection assembly 400 and the interchangeable member 500. The processing module 200 is disposed in the outer shell member 100, and stores a component definition table which records a plurality of pieces of identification data, and a plurality of pieces of working mode data corresponding to the plurality pieces of identification data.

The power supply module 300 is disposed in the outer shell member 100 and electrically coupled to the processing module 200. The difference between the first aspect and the second aspect of the multifunctional electronic cigarette of the present disclosure is that the second aspect of the multifunctional electronic cigarette includes the at least one data transmission line 600 which has an end electrically coupled to the processing module 200.

The connection assembly 400 is electrically coupled to the power supply module 300 and the processing module 200, fixed at and exposed out of an end of the outer shell member 100. As shown in FIG. 5, the connection assembly 400 includes an engagement part 401, and at least one transmission part 410 electrically coupled to the other end of the data transmission line 600.

The interchangeable member 500 and the engagement part 401 can be assembled with each other by a rotation manner, for example, the interchangeable member 500 may have one of outer thread and inner thread, and the engagement part 401 may have the other, and the interchangeable member 500 and the connection assembly 400 can be rotated to combine with each other through the outer thread and the inner thread. Preferably, the interchangeable member 500 can include the E-liquid cassette 510 having the atomizing component, the alcohol detecting device 520, the LED device or a laser device.

The identification data of the interchangeable member 500 can be transmitted to the processing module 200 through the transmission part 410 and the data transmission line 600, and the processing module 200 then checks whether the received identification data matches one of the plurality pieces of the restored identification data, and if yes, the processing module 200 can determine the type of the interchangeable member 500 and then execute the working mode data corresponding to the determined type, thereby generating the appropriate operation voltage and current for the interchangeable member 500. Preferably, the working mode data includes variations in strength or frequency of the operation voltage and current. Furthermore, the interchangeable member 500 may include the EGO connector or the 510 connector, so that the interchangeable member 500 may be easily assembled with the engagement part 401 rotatably. After the interchangeable member 500 is combined with the connection assembly 400, the interchangeable member 500 can transmit the identification data thereof to the processing module 200 through the transmission part 410 and the data transmission line 600.

For example, when the interchangeable member 500 is the laser device, the laser device can transmit the identification data thereof to the processing module 200, so that the processing module 200 can compare the received identification data with the plurality of pieces of pre-stored identification data to determine that the interchangeable member 500 is the laser device, and then drive and control the laser device by the correct manner, for example, after the laser device is combined with the connection assembly 400, the processing module 200 can provide the user to control the laser device to emit light.

When the interchangeable member 500 includes the E-liquid cassette 510 having the atomizing component, the function of controlling the electronic cigarette may include temperature detection for atomizing the E-liquid contained in the E-liquid cassette 510. As a result, the interchangeable member 500 may include different devices, so the processing module 200 must be able to control the interchangeable member 500 by the correct manner according to the identification data transmitted from the interchangeable member 500.

Similarly, when the interchangeable member 500 includes the alcohol detecting device 520, the alcohol detecting device 520 can be assembled with the connection assembly 400 to form an alcohol detector, and the power supply module 300 provides power to the alcohol detecting device 520, so that the user can blow into the alcohol detecting device 520 to detect the user's blood alcohol concentration. Similarly, when the interchangeable member 500 includes the LED device, the LED device can be assembled with the connection assembly 400 to form the LED flashlight for illumination.

The following describes operation of the multifunctional electronic cigarette of the present disclosure.

The processing module 200 of the present disclosure can pre-store the plurality of device driver programs, and select and execute one of the plurality of device driver programs according to the received identification data, thereby controlling the power supply module 300 to output appropriate operation voltage and current. For example, the processing module 200 can store driver programs of the E-liquid cassette 510, the alcohol detecting device 520, the LED device and the laser device in advance, and the processing module 200 can execute each driver program to control the power supply module 300 to output appropriate operation voltage and current. Furthermore, when the multifunctional electronic cigarette of the present disclosure includes a button or a screen, the processing module 200 can execute the driver program to perform a corresponding function when the button on the outer shell member 100 is pressed, or display information on the screen.

As a result, the user just needs to carry the multifunctional electronic cigarette of the present disclosure and other interchangeable members 500, and replaces the interchangeable member 500 to execute a specific function upon demand. As a result, it is more convenient for the user to operate the multifunctional electronic cigarette of the present disclosure for multiple purposes. For example, when the user attends party at smoking and drinking occasion at night, the user can carry the multifunctional electronic cigarette of the present disclosure, the E-liquid cassette 510, the alcohol detecting device 520 and the LED device. At the smoking occasion, the user can assemble the E-liquid cassette 510 with the connection assembly 400, and the processing module 200 can identify and drive the E-liquid cassette 510, so that the user can vape the electronic cigarette. After the user drinks alcoholic beverages, the user can assemble the alcohol detecting device 520 and the connection assembly 400, and the processing module 200 can identify and drive the alcohol detecting device 520 to check whether the user's blood alcohol concentration exceeds the legal limit. For illumination, the user can assemble the LED device and the connection assembly 400, and the processing module 200 can identify and drive the LED device.

Furthermore, in order to smoothly communicate the processing module 200 with the different interchangeable members 500, the multifunctional electronic cigarette of the present disclosure can use a communication protocol for communication between the interchangeable member 500 and the processing module 200. The communication protocol may include 1-Wire communication protocol, inter-integrated circuit bus($I^2C$) protocol, and server message block(SMB) protocol and so on. The processing module 200 can communicate with the interchangeable member 500 based on the communication protocol, thereby facilitating to improve extendibility of the multifunctional electronic cigarette.

In a third aspect, the present disclosure provides a multifunctional portable electronic device including: an outer shell member 100; a processing module 200 disposed in the outer shell member; a power supply module 300 disposed in the outer shell member 100 and electrically coupled to the processing module 200; a connection assembly 400 electrically coupled to the power supply module 300 and the processing module 200, and fixed on and exposed out of an end of the outer shell member 100; and a plurality of interchangeable members 500 selectively coupled to the connection assembly 400 electrically, and including at least two of an E-liquid cassette having an atomizing component, an alcohol detecting device, and a LED device.

In a detection mode, the processing module calculates an operational resistance of one of the plurality of the interchangeable members which is coupled to the connection assembly, and then controls, in a normal operation mode, the power supply module to generate operation voltage and current according to the operational resistance. The operational resistance is resistance of the interchangeable member which is executing a main operational function thereof.

According to an embodiment, the interchangeable members 500 may include the alcohol detecting device and the LED device, and the user can selectively assemble the alcohol detecting device with the connection assembly 400 to form an alcohol detector, or assemble the LED device with the connection assembly 400 to form a LED flashlight.

The present disclosure disclosed herein has been described by means of specific embodiments. However, numerous modifications, variations and enhancements can be made thereto by those skilled in the art without departing from the spirit and scope of the invention set forth in the claims.

What is claimed is:

1. A multifunctional electronic cigarette, comprising: an outer shell member;
a processing module disposed in the outer shell member;
a power supply module disposed in the outer shell member and electrically coupled to the processing module;
a connection assembly electrically coupled to the power supply module and the processing module, and fixed on and exposed out of an end of the outer shell member; and an interchangeable member electrically coupled to the connection assembly, and comprising one of an E-liquid cassette having an atomizing component, an alcohol detecting device and a LED device;
wherein, the processing module is configured to control the power supply module to respectively apply an initial voltage and a test voltage to the connection assembly in sequential order, and calculate an operational resistance of the interchangeable member during the process of applying voltages, and then control the power supply module to generate operation voltage and current to the interchangeable member according to the operational resistance;
wherein the operational resistance is resistance of the interchangeable member which is executing a main operational function thereof.

2. The multifunctional electronic cigarette according to claim 1, wherein during the process of applying the voltage form the initial voltage to the test voltage, the operational resistance of the LED device is dropped after the voltage exceeds a barrier voltage which has a value between the initial voltage and the test voltage.

3. The multifunctional electronic cigarette according to claim 1, wherein the operational resistance of the alcohol detecting device is higher than that of the E-liquid cassette.

4. The multifunctional electronic cigarette according to claim 1, wherein the connection assembly comprises an EGO connector or a 510 connector.

5. The multifunctional electronic cigarette according to claim 1, wherein the processing module stores a plurality of resistance ranges and a plurality of device driver programs respectively corresponding to the plurality of resistance ranges, and the processing module selects and executes one of the plurality of device driver programs according to the operational resistance and the plurality of resistance ranges, thereby controlling the power supply module to output the operation voltage and current.

6. The multifunctional electronic cigarette according to claim 1, wherein the alcohol detecting device generates different sensing resistances for different blood alcohol concentrations.

7. A multifunctional electronic cigarette, comprising: an outer shell member;
a processing module disposed in the outer shell member and configured to store a component definition table which records identification data and working mode data corresponding to the identification data;
a power supply module disposed in the outer shell member and electrically coupled to the processing module;
at least one data transmission line comprising an end electrically coupled to the processing module;
a connection assembly electrically coupled to the power supply module and the processing module, fixed on and expose out of an end of the outer shell member, and comprising at least one transmission part and an engagement part, wherein the at least one transmission part is connected with other end of the data transmission line; and
an interchangeable member combined with the engagement part to connect with the connection assembly by a rotation manner, and comprising one of an E-liquid cassette which has an atomizing component, an alcohol detecting device, a LED device, and a laser device;
wherein the processing module receives identification data of the interchangeable member through the at least one transmission part and the data transmission line, and the processing module compares the received identification data with the stored identification data to determine a type of the interchangeable member, and the processing module executes the working mode data corresponding to the determined type, to generate operation voltage and current for the interchangeable member.

8. The multifunctional electronic cigarette according to claim 7, wherein the working mode data comprises variations in strength and frequency of the operation voltage and current.

9. The multifunctional electronic cigarette according to claim 7, wherein the interchangeable member and the processing module are in communication with each other by a communication protocol.

10. The multifunctional electronic cigarette according to claim 7, wherein the processing module stores a plurality of resistance range and a plurality of device driver programs respectively corresponding to the plurality of resistance range, and the processing module selects and executes one of the plurality of device driver programs according to the operational resistance and the plurality of resistance ranges, thereby controlling the power supply module to output the operation voltage and current.

11. A multifunctional portable electronic device, comprising: an outer shell member;
a processing module disposed in the outer shell member;
a power supply module disposed in the outer shell member and electrically coupled to the processing module;
a connection assembly electrically coupled to the power supply module and the processing module, and fixed on and exposed out of an end of the outer shell member; and a plurality of interchangeable members selectively coupled to the connection assembly electrically, and comprising at least two of an E-liquid cassette having an atomizing component, an alcohol detecting device, and a LED device;
wherein, in a detection mode, the processing module calculates an operational resistance of one of the plurality of the interchangeable members which is coupled to the connection assembly, and then controls, in a normal operation mode, the power supply module to generate operation voltage and current according to the operational resistance;
wherein the operational resistance is resistance of the interchangeable member which is executing a main operational function thereof.

12. The multifunctional portable electronic device according to claim 11, wherein in the detection mode, the processing module controls the power supply module to respectively apply an initial voltage and a test voltage to the connection assembly in sequential order for calculation of the operational resistance.

13. The multifunctional portable electronic device according to claim 11, wherein the operational resistance of the alcohol detecting device is higher than that of the E-liquid cassette.

14. The multifunctional portable electronic device according to claim 11, wherein the connection assembly comprises an EGO connector or a 510 connector.

* * * * *